United States Patent [19]

Matsumura et al.

[11] 4,198,144

[45] Apr. 15, 1980

[54] EYE FUNDUS CAMERA

[75] Inventors: Isao Matsumura; Yoshimi Kohayakawa, both of Yokohama, Japan

[73] Assignee: Canon Kabushiki Kaisha, Tokyo, Japan

[21] Appl. No.: 949,556

[22] Filed: Oct. 10, 1978

Related U.S. Application Data

[63] Continuation of Ser. No. 782,711, Mar. 30, 1977, abandoned.

[30] Foreign Application Priority Data

Apr. 1, 1976 [JP] Japan ................................ 51-36261

[51] Int. Cl.² .......................... G03B 29/00; A61B 3/10
[52] U.S. Cl. .......................................... 354/62; 351/6
[58] Field of Search ......................... 354/62, 152, 155; 351/6, 7

[56] References Cited

U.S. PATENT DOCUMENTS

| | | | |
|---|---|---|---|
| 2,940,371 | 6/1960 | Thurow | 354/62 X |
| 3,003,387 | 10/1961 | Schiele | 354/155 X |
| 3,016,000 | 1/1962 | Noyori | 354/62 |
| 3,572,909 | 3/1971 | Van Patten et al. | 351/6 |
| 3,914,032 | 10/1975 | Takano et al. | 351/6 X |
| 3,925,793 | 12/1975 | Matsumura et al. | 354/62 |
| 3,936,844 | 2/1976 | Matsumura | 354/62 |
| 3,986,030 | 10/1976 | Teltscher | 351/7 X |

*Primary Examiner*—Donald A. Griffin
*Attorney, Agent, or Firm*—Toren, McGeady and Stanger

[57] ABSTRACT

An eye fundus camera permitting simple focusing is disclosed. An optical system with a microprism projects an image of a focusing mark on the eye fundus.

When the mark image formed on the eye fundus is not just focused, this mark image is divided and separated into at least three directions. An objective lens forms the image which is formed on the eye fundus on a recording film and cooperates with the projection lens of the mark projection optics. Therefore, the objective lens can be focused by observing the mark image which is formed on the eye fundus.

8 Claims, 17 Drawing Figures

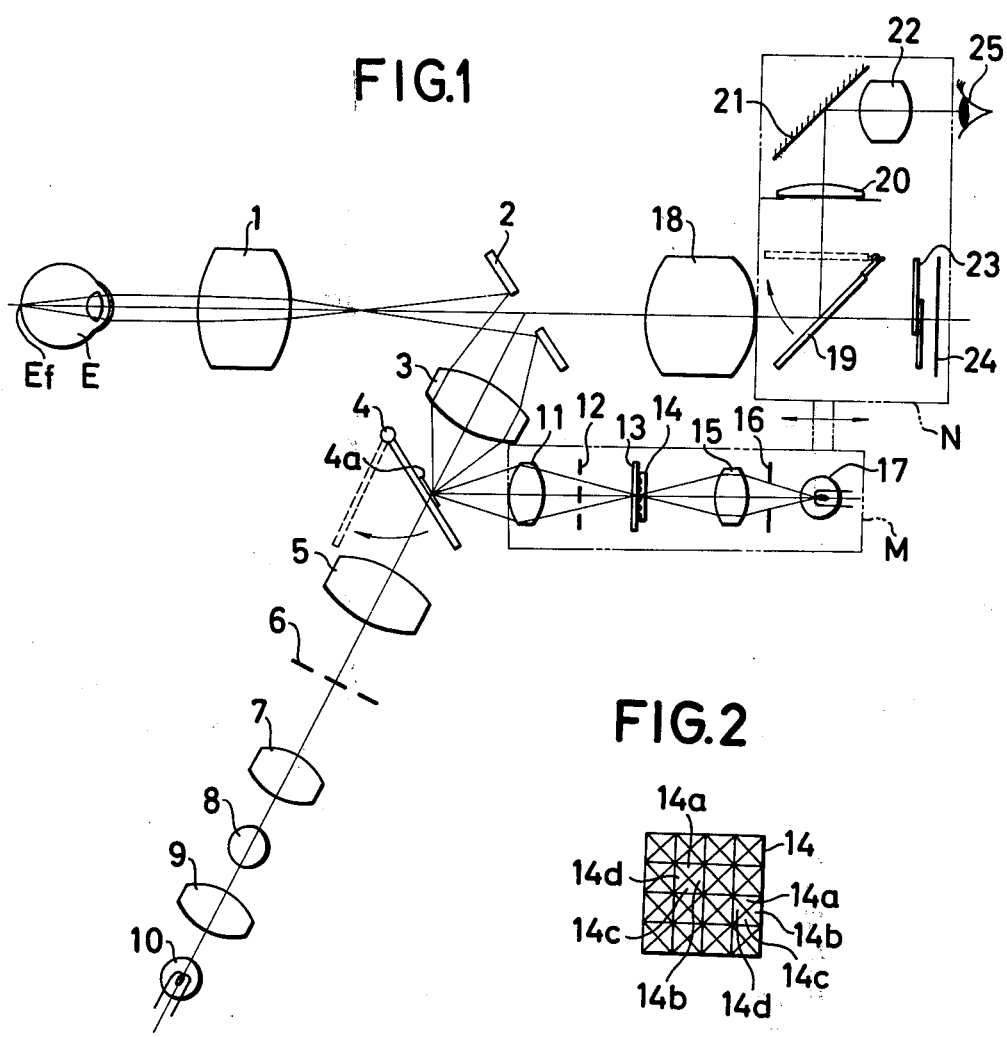

EYE FUNDUS CAMERA

This is a continuation of Application Ser. No. 782,711, filed Mar. 30, 1977 and now abandoned.

BACKGROUND OF THE INVENTION

1. Field of the Invention

The present invention relates to an eye fundus camera, particularly an eye fundus camera in which the focus setting for the objective lens which forms an image of the eye fundus on the recording medium can be carried out facilely.

2. Description of the Prior Art

U.S. Pat. No. 3,925,793, discloses an eye fundus camera which permits simple focusing. In this camera, the objective lens which forms the image of the eye fundus on the film cooperates with the projection lens which directs two beams to the eye fundus. These two beams are obtained by two wedge prisms and the mark means having a slit opening, this mark means and these two wedge prisms being on a position which is substantially equal to the film with respect to the eye fundus, and these two beams form two spots on the eye fundus. The beam of slit-like cross section from the slit opening is divided by the two wedge prisms into two beams having a symmetrical angle to the optical axis, and these two beams are again made into a beam of slit-like cross section on the conjugate plane, and they become two beams separate in two directions on a non-conjugate plane.

Therefore, when the eye fundus is conjugate to the mark means, a beam of slit-like cross section can be obtained, and two beams divided into two directions are obtained when the eye fundus is not conjugate to the mark means.

SUMMARY OF THE INVENTION

The object of the present invention is to provide the improved eye fundus camera where the focus setting can be carried out facilely.

In other words, according to the fundus camera disclosed in the above-mentioned U.S. Patent, the two beams are directed to the eye fundus where two spots on the eye fundus move separately in two directions when the focus setting is wrong, but according to the present eye fundus camera, three or more beams are directed to the eye fundus, and these beams move in a number of directions corresponding to the number of beams.

So that, according to the desirable embodiment of the present invention, the so-called micro prism which is formed of many triangular pyramids, many square pyramids, many pentagonal pyramids, and many hexagonal pyramids are arranged in front of the mark means or behind said mark means. Many beams (three or more) which have a different angle with respect to the optical axis of the camera are generated by said micro prism, and said beams are directed into the eye fundus. Therefore, the situation which is focused or defocused can be distinguished easily.

BRIEF DESCRIPTION OF THE DRAWINGS

FIG. 1 is a cross sectional view illustrating the embodiment of the present invention.

FIG. 2 is a plane view of the micro prism which is an essential construction of the embodiment.

FIG. 3 is a plane view of the mark means.

FIG. 4 is a plane view of the ring slit plate.

FIG. 5 is a view showing the interaction of the ring slit plate and the micro prism.

FIG. 6 is a plane view of the reflection plate.

DETAILED DESCRIPTION OF THE PRESENT EMBODIMENT

Figure 7:
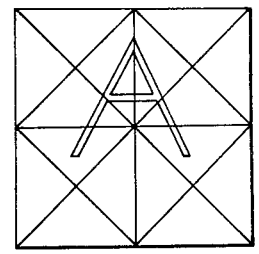
FIG. 7, FIG. 8, FIG. 9 and FIG. 10 are views illustrating the correspondence of the focusing conditions to the mark images.

In FIG. 1, E is an eye to be examined, and Ef is an eye fundus. Element 1 is an objective lens of the eye fundus camera. A mirror 2 with a circle opening in the center is used to direct illumination light to the eye fundus and to remove the reflecting light from the cornea. Element 3 is a first relay lens, and 5 is a second relay lens. A swing up transparent member 4 has a small mirror 4a as shown in FIG. 6, for directing the luminous flux from a mark projector unit M to the eye fundus during focusing of the objective lens 1. The member 4 moves from the optical path when a photograph is taken. A ring slit plate 6 with an opening cooperates with the mirror 2 and is used to remove the reflecting light on the cornea as well-known. A condenser lens 7 causes convergence of the luminous flux from a strobo tube 8 and a tunsten lamp 10 on the right slit plate 6. Another condenser lens 6 applies the image of the lamp 10 on the strobo tube 8. The members 3 to 10 from an illuminating unit.

Figure 14:
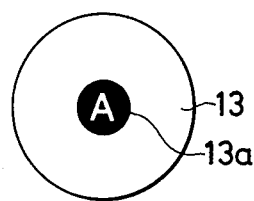
FIG. 14 is a plane view of the mark means.

Member 11 is a relay lens, and 12 is a light shielding plate having a ring transmitting part as shown in FIG. 14. A mark plate 13 includes a transparent part 13b and a light shielding part 13a as shown in FIG. 3. A micro prism plate 14 composed of square pyramids or the hexagonal pyramid is arranged close to the mark plate 13. A condenser lens 15 causes convergence of light coming from a tunsten lamp 17 and passing through an aperture diaphragm plate 16 onto the mark plate 13. The aperture diaphragm plate 16 is placed in conjugate relation with the light shielding plate 12, the condenser lens 15, the mark plate 13 and the prism plate 14. The elements 11 to 17 form the mark projector unit M, and this unit M is movable along the axis.

Further, element 18 is a photographic lens, 19 is a turning mirror, 20 is a field lens, 21 is a reflecting mirror, 22 is an eyepiece, 23 is a shutter, 24 is a film surface and 25 is an eye of examiner. These elements of numerals from 19 to 24 form a unit N which is movable along the axis. The unit N is linked with the unit M, so that the mark plate 13 and the film 24 are substantially in equal relationship with respect to the eye fundus.

In to the above-mentioned device, the eye fundus is illuminated by the light of the tungsten lamp 10 during observation. That is, the light from the lamp 10 forms the image on the ring slit plate 6 with the condenser lens 9 and 7. The light from the ring slit plate 6 is directed to the eye by the relay lenses 5, 3, 1 and the mirror, so as to form an image of the ring slit plate 6 on the cornea of the eye E. The objective lens 1 receives the light reflected by the eye fundus Ef and transmitted through the pupil of the eye E examined, and forms the image of the eye fundus. The image of the eye fundus is relayed to the film surface by said photographic lens 18 through the mirror 2. The turning mirror 19 reflects the axis during observation. This turning mirror guides the light from the eye fundus to the finder part, namely the field lens 20, the reflecting mirror 21, the eyepiece 22, and the eye 25 of the examiner, so that the eye fundus is observed by the examiner.

Meanwhile, the light from the illumination lamp 17 of said mark projector unit M illuminates the mark plate 13 through the condenser lens 15 and the micro prism 14. The micro prism is used to divide the illumination beam into more than three beams, and to bend the divided beams to directions corresponding to the angles of the prism.

The light beams coming from said mark plate 13 and the micro prism 14 are directed to said light shielding plate 12 which is conjugate with the mirror 2 with respect to said relay lens 3 and 11. As these beams coming from the mark plate 13 are bent into four directions by a square pyramid micro prism (14a, 14b, 14c and 14d) as shown in FIG. 2, four beams (12a, 12b, 12c and 12d) which are equal to the number of angularities of the prism arrive on the light shielding plate 12 as shown in FIG. 4.

Therefore, the four beams are restricted by the shielding part of the light shielding plate 12 and pass the part of the oblique lines as shown in FIG. 5. These four beams form the image of the mark 13 on the small mirror 4a by the lens 11. The image of the mark 13 is relayed to the conjugate plane positioned between the mirror 2 and the lens 1 by the lens 3 through the mirror 2. The four light beams coming from the relayed image of the mark plate 13 arrive at the eye fundus Ef of the eye E examined. As above-mentioned, the image of the mark 13b is formed on the eye fundus Ef, but when the image is defocused, the image is divided into four parts.

Figure 8:
Figure 9:
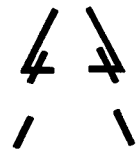
Figure 10:
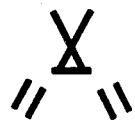

FIG. 8 to FIG. 10 show the images of the mark plate 13 formed on the eye fundus. It is assumed here, that the square pyramids of said micro prism are almost the same size as the mark shown in FIG. 7.

In FIG. 8, if the mark plate 13 is conjugate with the eye fundus, the mark image is formed on the eye fundus in its original form. If not in a conjugate relation, the image is divided into four part as shown in FIG. 9 and FIG. 10.

Therefore, whether the mark image is the same as the original form or not, the examiner 25 can adjust the unit M and N simultaneously until the image is focused.

Figure 11:
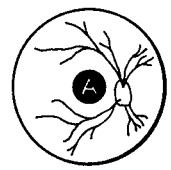
FIG. 11 is a view illustrating the view when one looked through the finder.

FIG. 11 shows the finder field in which the image of the focused mark and the eye fundus can be seen. When the examiner presses the release button (not shown), the reflecting plate 4 and the turning mirror 19 swing up, the strobo tube 8 fires, and the shutter 23 opens. The image on the eye fundus is then photographed on the film surface 24. At this time, as the light from the mark projector unit M is removed from the light path, so the image on the mark is not photographed on the film surface. In the aforementioned device, the film surface 24 and the mark plate 13 are moved along the axis for focusing. However, according to another embodiment, the focusing can be done by moving the lens 18, and 21 along the axis. By arranging an infrared light—visible light converter at the field lens 20 and an infrared filter in front of the lamp 10 and 17, the focusing is performed under infrared light and recording is done in visible light. In this embodiment, by using a dichroic mirror, swing up mirror 19 and 4 are removed.

Figure 12:
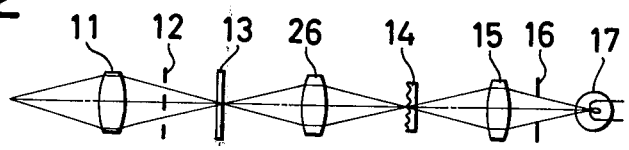
FIG. 12 is a view of the another embodiment of the mark projector unit.

Further, in the present embodiment, the mark plate 13 and the micro prism plate 14 in the mark projector are arranged closely. However, in the embodiment shown in FIG. 12, by projecting the image of the micro prism 14 on the mark plate 13 with the relay lens 26, same effect is obtained.

Figure 13:
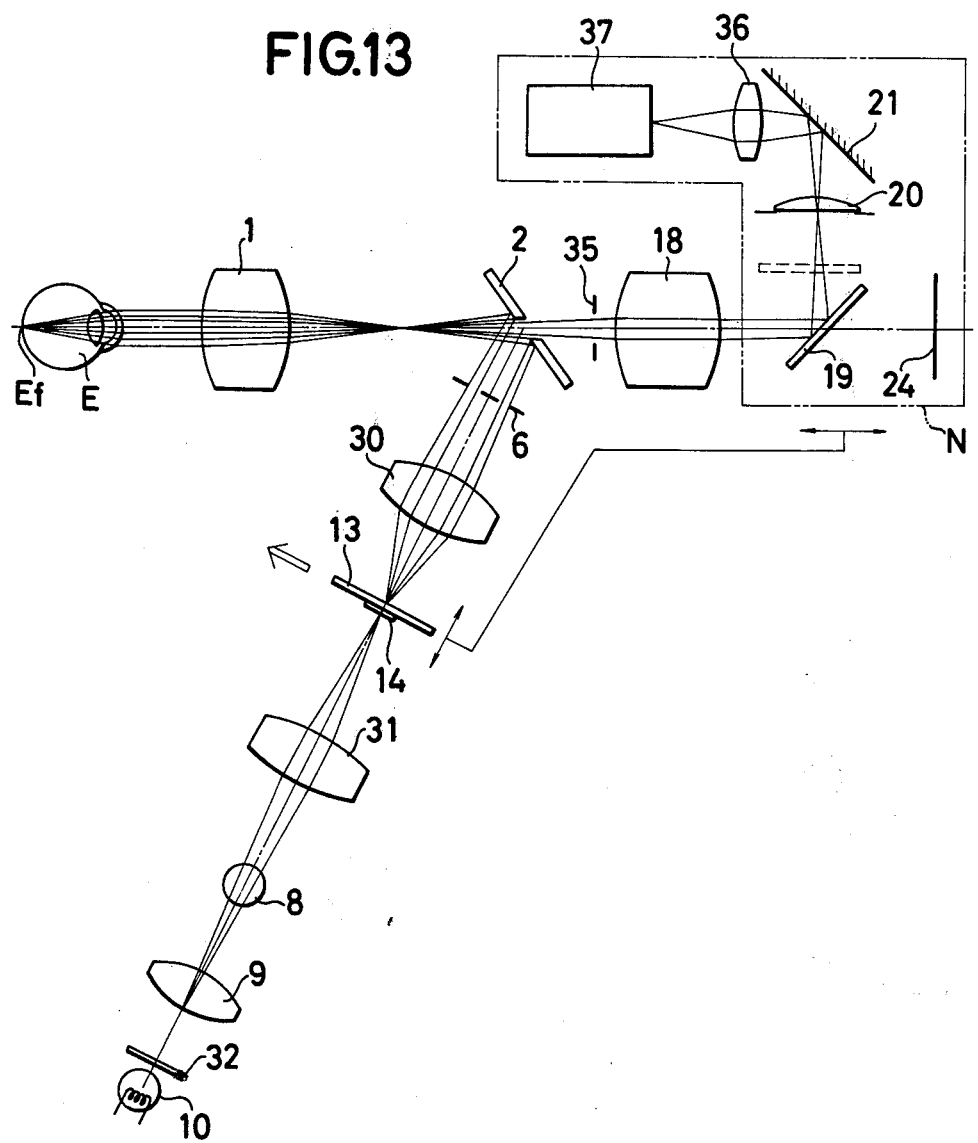
FIG. 13 is a cross sectional view showing another embodiment.

FIG. 13 shows another embodiment of the present invention. In this drawing, the same members as in the embodiment of FIG. 1 are represented by like reference characters. Here if the system is focused, the mark plate 13 and the eye fundus Ef are conjugate with respect to a relay lens 30 and the objective lens 1. A condenser lens, 21 forms images of the strobo tube 8 and the tungsten lamp 10 on the mark plate 13 and the micro prism plate 14. Element 32 is an infrared or a near infrared filter. A circle opening plate, 35 removes the reflected light from the cornea in cooperation; with the ring slit plate 6. Element 36 is a photographic lens, and element 37 is an infrared image pickup tube connected with a monitor (not shown).

Figure 15:
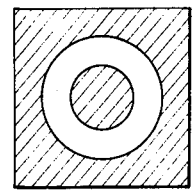
FIG. 15 is a plane view of the ring slit plate.
Figure 16:
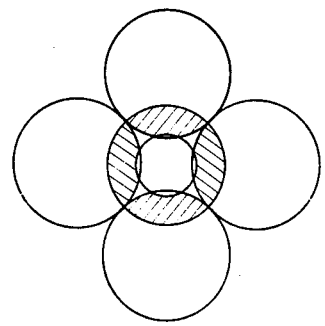
FIG. 16 is a view showing the interaction of the ring slit plate and the micro prism.

In the device as above-mentioned, the light flux from the lamp 10 is divided into the plural fluxes (if the micro prism is a square pyramid, it is divided into four parts) by the micro prism plate 14, and illuminates the mark plate 6. FIG. 15 is a plan view illustrating the ring slit plate 6. The light fluxes passing through this ring slit are shown in FIG. 16. The four light beams coming from the ring slit plate 6 enter the eye fundus.

Figure 17:
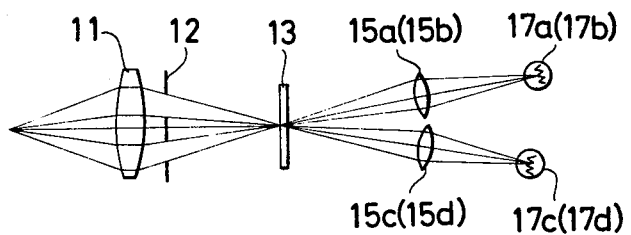
FIG. 17 is an illustration to compare the mark projection units.

FIG. 17 shows another embodiment of the mark projector unit N of FIG. 1, in which the mark plate 13 is illuminated with four beams.

What is claimed is:
1. An eye fundus camera comprising:
a photographic system including holding means and an objective lens,
said holding means defining a plane at which a recording medium is to be mounted,
said objective lens forming an image of an eye fundus on the plane,
a focusable projector defining an optical axis for projecting at least three beams having equivalent angles with the optical axis of the objective lens upon the eye fundus at different directions of incidence to form spots,
coupling means for focusing the photographic system while focusing said projector so that when the eye fundus has a conjugate relation with the plane, the spots formed on the eye fundus by these beams exhibit a predetermined arrangement and when the eye fundus is not conjugate with the plane, the spots exhibit another arrangement, and
an observing device for observing the arrangement of the spots formed on the eye fundus.
2. An eye fundus camera according to claim 1, in which said projector includes a mark means having an opening that is positioned on the same plane of said recording medium substantially and in which a micro prism plate is arranged in adjacent with said mark means.
3. A camera as in claim 2, wherein the projector includes a projection lens and said projection lens is moved with one of said holding means and the objective lens during focusing of said projector.

4. An eye fundus camera according to claim 1 in which said projector includes a mark means having an opening that is positioned on the same plane of the recording medium substantially and illuminated by at least three beams of different directions.

5. A camera as in claim 4, wherein the projector includes a projection lens and said projection lens is moved with one of said holding means and the objective lens during focusing of said projector.

6. An eye fundus camera according to claim 1, in which said projector includes an infrared light source for forming the beams and said observation device includes means in the path of light from the objective lens for converting infrared light to the visible light.

7. A camera as in claim 6, wherein the projector includes a projection lens and said projection lens is moved with one of said holding means and the objective lens during focusing of said projector.

8. A camera as in claim 1, wherein the projector includes a projection lens and said projection lens is moved with one of said holding means and the objective lens during focusing of said projector.